US006789539B2

(12) United States Patent
Martinez

(10) Patent No.: US 6,789,539 B2
(45) Date of Patent: Sep. 14, 2004

(54) DILUTION REGULATION METHOD AND DEVICE FOR BREATHING APPARATUS

(75) Inventor: Patrice Martinez, Le Perray en Yvelines (FR)

(73) Assignee: Intertechnique, Plaisir (FR)

( * ) Notice: Subject to any disclaimer, the term of this patent is extended or adjusted under 35 U.S.C. 154(b) by 0 days.

(21) Appl. No.: 10/256,943

(22) Filed: Sep. 27, 2002

(65) Prior Publication Data

US 2003/0084901 A1 May 8, 2003

(30) Foreign Application Priority Data

Nov. 8, 2001 (FR) ............................................ 01 14452

(51) Int. Cl.[7] ............................................... A61M 16/00
(52) U.S. Cl. .............................. 128/204.26; 128/204.21
(58) Field of Search ....................... 128/200.24, 204.18, 128/204.19, 204.21–204.23, 204.25, 204.26, 204.27, 204.29, 205.11, 205.23, 205.24

(56) References Cited

U.S. PATENT DOCUMENTS 4,282,870 A * 8/1981 Porlier .................. 128/203.14
4,648,397 A 3/1987 Beale
4,651,728 A 3/1987 Gupta et al.
4,664,108 A 5/1987 Ansite
4,823,788 A 4/1989 Smith et al.
4,856,507 A * 8/1989 Ouillon et al. ......... 128/204.26
4,928,682 A 5/1990 Stevenson et al.
5,269,295 A * 12/1993 Foote et al. ........... 128/204.18
5,318,019 A 6/1994 Celaya
5,351,682 A * 10/1994 Foote .................... 128/205.24
5,460,175 A * 10/1995 Foote et al. ........... 128/205.24
5,645,055 A * 7/1997 Danon ................... 128/204.25
5,701,889 A * 12/1997 Danon ................... 128/204.29
5,799,652 A 9/1998 Kotliar
5,881,725 A * 3/1999 Hoffman et al. ....... 128/204.26
5,961,442 A * 10/1999 Meckes ....................... 600/20

* cited by examiner

*Primary Examiner*—Weilun Lo
*Assistant Examiner*—Teena Mitchell
(74) *Attorney, Agent, or Firm*—Dean W. Russell; Kilpatrick Stockton LLP

(57) ABSTRACT

In a method of regulating the flow rate of additional oxygen taken from a pressurized inlet for oxygen from a source and admitted into a breathing mask provided with an inlet for dilution ambient air, the ambient pressure and the instantaneous inhaled breathe-in flow rate in terms of volume reduced to ambient conditions are measured in real time. The minimum oxygen content in the complete inhalation phase in order to comply with respiratory standards is computed from the ambient pressure and the instantaneous flow rate of additional oxygen is controlled in such a manner as to satisfy the requirements of the applicable standards with a safety margin that is generally a few percent. There is also described a regulator implementing the above method.

11 Claims, 3 Drawing Sheets

DILUTION REGULATION METHOD AND DEVICE FOR BREATHING APPARATUS

CROSS-REFERENCE TO RELATED APPLICATIONS

This application claims priority to French Patent Application No. 0114452 filed in the French Patent Office on Nov. 8, 2001, the entire contents of which are incorporated by reference herein.

FIELD OF THE INVENTION

The present invention relates in general manner to demand regulators with dilution by ambient air for supplying breathing gas to satisfy the needs of a wearer of a mask, using feed from a source of pure oxygen (oxygen cylinder, chemical generator, or liquid oxygen converter) or of gas that is highly enriched in oxygen, such as an on-board oxygen generator system (OBOGS). The invention also relates to individual breathing apparatuses including such regulators.

The invention relates particularly to regulation methods and devices for breathing apparatuses for use by the crew of civil or military aircraft who, above a determined cabin altitude, need to receive breathing gas providing oxygen at at least a minimum flow rate that is a function of altitude, or providing, on each intake of breath, a quantity of oxygen that corresponds to a minimum concentration for oxygen in the inhaled mixture. The minimum rate at which oxygen must be supplied is set by standards, and for civil aviation these standards are set by the Federal Aviation Regulations (FAR).

BACKGROUND OF THE INVENTION

Present demand regulators can be carried by a mask; this is the usual case in civil aviation, unlike combat aircraft where the regulator is often situated on the wearer's seat. Such regulators have an oxygen feed circuit connecting an inlet for oxygen under pressure to an admission to the mask, and including a main valve, generally controlled pneumatically by a pilot valve, and a circuit for supplying dilution air taken from the ambient atmosphere. Oxygen inflow is started and stopped in response to the wearer of the mask breathing in and breathing out, in response to the altitude of the cabin, and possibly also in response to the position of selector means that can be actuated by hand for enabling normal operation with dilution, operation in which oxygen is fed without dilution, and operation at high pressure. Regulators of that type are described in particular in document FR-A-2 778 575, to which reference can be made.

Those known regulators are robust, they operate reliably, and they can be made in relatively simple manner even for large breathe-in flow rates. However in order to be able under all operating conditions to comply with the minimum flow rates for oxygen (taken from the pure oxygen feed and from the dilution air), they suffer from the drawback that it is necessary to make them in such a manner that over the major portion of their operating range they draw pure oxygen at a rate that is well above the rate that is actually necessary. This requires an aircraft to carry an on-board volume of oxygen that is in excess of real physiological needs, or else it requires the presence of an on-board generator of performance that is higher than absolutely essential.

Proposals have also been made for an electronically-controlled regulator for feeding the breathing mask of a fighter pilot (patents FR 79/11072 and U.S. Pat. No. 4,336,590). That regulator makes use of pressure sensors and electronics that control an electrically-controlled valve for adjusting the rate at which oxygen is delivered. Dilution air is sucked in via a Venturi. The electronically-controlled regulator has the advantage of enabling the rate at which pure oxygen is supplied to be matched better with physiological requirements. However it suffers from various limitations. In particular, dilution depends on the operation of an ejector. The way in which the pure oxygen flow rate and the dilution air flow rate are controlled means that when controlling the flow rate of pure oxygen it is difficult to take account of the oxygen brought in by the dilution air since its flow rate is itself a function of the oxygen flow rate and of other state parameters (in particular the breathe-in demand from the wearer). In most cases, the flow rate of pure oxygen will be at a level that leads to excess oxygen being supplied to the wearer, and no provision is made to use the electronic control system in such a manner as to obtain operation that makes it possible under all conditions to supply an oxygen flow rate which is as close as possible to the minimum required by regulations.

OBJECTS AND SUMMARY OF THE INVENTION

The present invention seeks in particular to provide a regulation method and device that are better than those known in the past at satisfying practical requirements; in particular it seeks to provide a regulator making it possible to cause the oxygen flow rate that is required from the source to come close to the flow rate that is actually needed.

For this purpose, the invention proposes an approach that is different from the approaches that have been adopted previously; it relies on acting in real time to estimate or measure the essential parameters that determine oxygen needs (cabin altitude, instantaneous volume flow rate being breathed in, reduced to cabin conditions, percentage of oxygen in the inhaled mixture as required by regulations where regulations exist and as required by physiological considerations, . . . ), and to deduce therefrom the instantaneous flow rate at which additional pure oxygen needs to be supplied at each instant.

Consequently, in one aspect of the invention, there is provided a method of regulating the flow rate of additional oxygen taken from a pressurized inlet for oxygen coming from a source and admitted into a breathing mask provided with an inlet for dilution ambient air, the method comprising:

- measuring in real time the ambient pressure and the instantaneous inhaled breathe-in flow rate in terms of volume reduced to ambient conditions (directly or by measuring the rate at which dilution air is inhaled into the mask, while making allowance for the additional oxygen);
- on the basis of the ambient pressure, determining the minimum oxygen content to be achieved in the inhalation cycle in order to comply with respiratory standards; and
- controlling said instantaneous flow rate of additional oxygen in such a manner as to satisfy the requirements of the applicable standards with a safety margin that is generally a few percent.

Provision can be made for the dilution air to be regulated by adjusting the flow section by means of an altimeter capsule and without using a Venturi. Regulation can also be performed by means of a controlled valve, again without an ejector, in which case the favorable characteristics of regulators that are purely pneumatic are associated with those of a known electronically-controlled regulator.

In a first implementation, the flow rate of additional oxygen continues to be estimated throughout the inhalation period. This leads to adjusting the total volume of additional oxygen supplied during the complete inhalation phase. In another implementation, which in theory enables even more oxygen to be saved, account is taken of the fact that the respiratory tract contains a volume that does not contribute to gas exchange. More precisely, the last fraction of the breathing mixture to be breathed in does not reach the pulmonary alveoli. It does no more than penetrate into the upper airways of the respiratory tract, from which it is expelled into the atmosphere during exhalation. In another implementation, the method makes use of this observation, e.g. by detecting the instant beyond which the instantaneous inhaled flow rate drops below a predetermined threshold which is taken to mark the beginning of the final stage of inhalation during which oxygen is no longer used, and then switching off the supply of additional oxygen.

In yet another implementation, which makes use of the above observation that best use is made of the additional oxygen which is delivered during an initial phase of the breathe-in cycle:

- an estimate is made at the end of each breathing cycle of the total quantity of oxygen that is going to be required during the following inhalation (e.g. by calculating an average over a plurality of preceding cycles); and
- the total required quantity of additional oxygen is delivered during an initial stage of inhalation.

A comparison is then performed during the following stage of the inhalation cycle between the evaluated standard cycle and the way in which the real cycle takes place; in the event of a difference leading to a requirement for more oxygen than that forecast, additional oxygen is supplied in a quantity that is determined as a function of that difference.

In all cases, once the quantity of oxygen required by physiological needs has been determined, a calculation is performed to determine the quantity of pure oxygen that needs to be added in forced manner to the oxygen contained in the air inhaled directly from the surrounding atmosphere at a rate which is generally not under control, which air contains oxygen at a concentration of 21% (or higher if a conditioned atmosphere is used).

The invention also provides a regulator device comprising:

- an oxygen feed circuit connecting a pressurized inlet for oxygen coming from a source and admitted into a breathing mask via a first electrically-controlled valve for directly controlling flow rate;
- a dilution circuit supplying air from the atmosphere directly to the mask;
- a breathe-out circuit including a breathe-out check valve connecting the mask to the atmosphere; and
- an electronic control circuit for opening the electrically-controlled valve for directly controlling flow rate as a function of signals supplied at least by a sensor of ambient atmospheric pressure and by a sensor of inhaled air flow rate or of inhaled total flow rate.

The air flow rate sensor may be embodied in various ways. For example it may be of a commercially-available type that generates a pressure drop. Such a sensor determines head loss on passing through a constriction and supplies a signal representative of flow rate. The sensor could also be of the hot-wire type.

Such a structure is "hybrid" in that it associates characteristics of a pneumatically-controlled regulator for air flow rate with the characteristics of electronic control for the flow rate of additional pure oxygen, thus making regulation more flexible.

The terms "oxygen under pressure" or "pure oxygen" should be understood as covering both pure oxygen as supplied from a cylinder, for example, and air that is highly enriched in oxygen, typically to above 90%. Under such circumstances, the actual content of oxygen in the enriched air constitutes an additional parameter for taking into account, and it needs to be measured.

The flow rate control valve may open progressively, or it may be of the "on/off" type, in which case it is controlled by an electrical signal carrying pulse width modulation, with an adjustable duty ratio and with a pulse frequency greater than 10 Hz.

The control relationship stored in the electronic circuit is such that in "normal" operation the regulator supplies a total flow rate of oxygen that is not less than that set by regulations for each cabin altitude, the total oxygen being taken both from the source and from the dilution air.

In general, regulators are designed to make it possible not only to perform normal operation with dilution, but also operation using a feed of expanded pure oxygen (so-called "100%" operation), or of pure oxygen at a determined pressure higher than that of the surrounding atmosphere (so-called "emergency" operation). These abnormal modes of operation are required in particular when it is necessary to take account of a risk of smoke or toxic gas being present in the surroundings. The electronic circuit may be designed to close the dilution valve under manual control or under automatic control. An additional electrically-controlled valve under manual and/or automatic control may be provided to maintain positive pressure in the mask by applying positive pressure on the breathe-out valve, thereby tending to close it.

The dilution valve is advantageously closed by means of a two-position electrically-controlled valve having one state which causes the dilution valve to be closed by bringing its seat against a shutter carried by an element responsive to the pressure of the ambient atmosphere, and another position which brings the dilution valve seat into a determined position enabling the flow rate of dilution air to be adjusted by moving or deforming the element.

The invention may be embodied in numerous ways. In particular, the various components of the regulator may be shared in various ways between a housing carried by the mask and a housing for storing the mask when not in use, or any other external housing, including an in-line housing, so that it remains directly accessible to the wearer of the mask. For example:

- the pure oxygen feed circuit may be located entirely in a housing fixed on a mask; or
- a portion of said circuit, and in particular the first electrically-controlled valve, may be integrated in a box for storing the mask ready for use.

BRIEF DESCRIPTION OF THE DRAWINGS

The above characteristics and others that can advantageously be used in association with preceding characteristics, but that can also be used independently, will appear better on reading the following description of particular embodiments, given as non-limiting examples. The description refers to the accompanying drawings, in which.

MORE DETAILED DESCRIPTION

Figure 1:
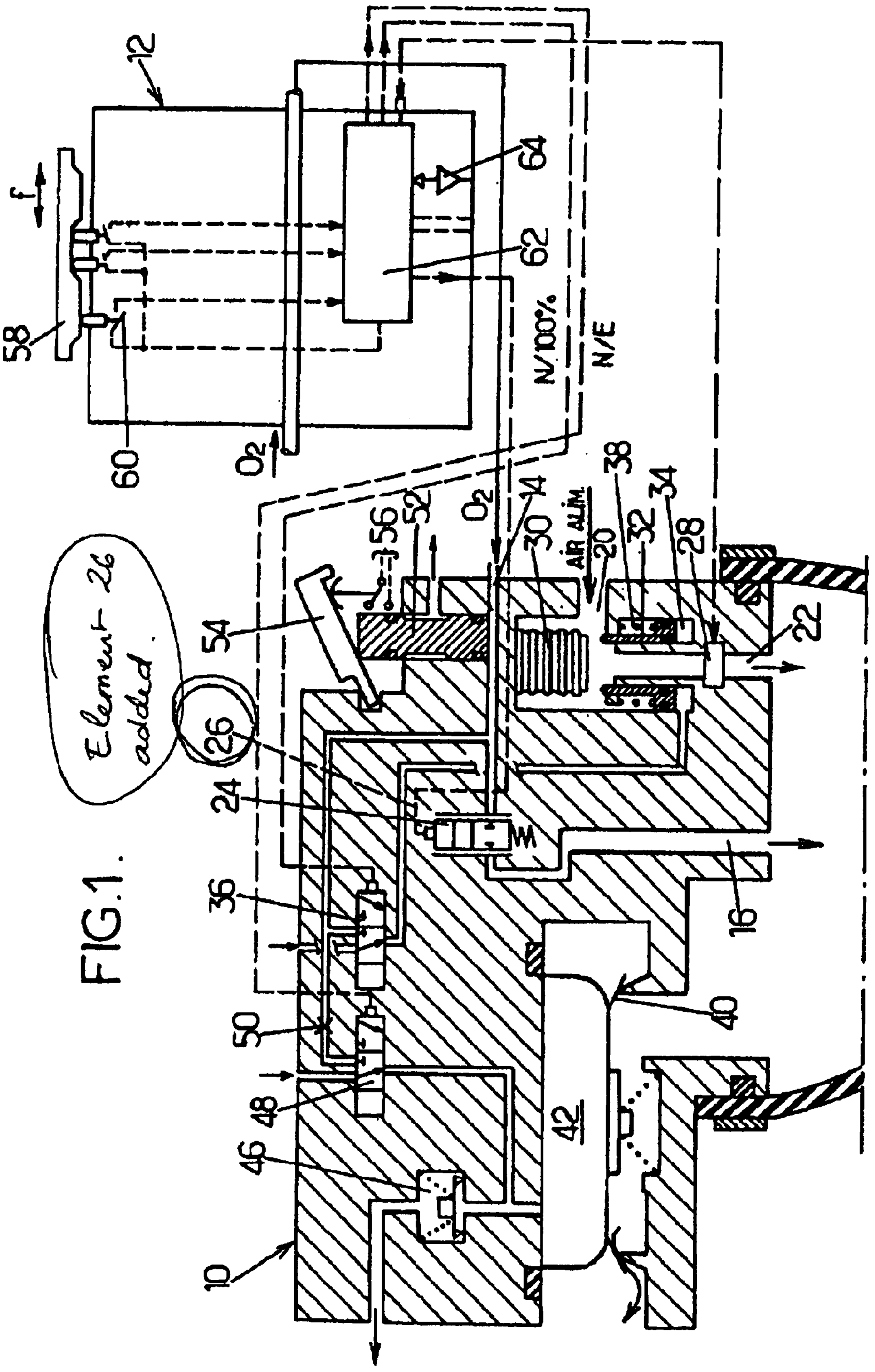
FIG. 1 is a pneumatic and electronic diagram showing the components involved by the invention in a regulator that can be referred to as an "integrated actuator" regulator.

The regulator shown in FIG. 1 comprises two portions, one portion 10 incorporated in a housing carried by a mask (not shown) and the other portion 12 carried by a box for storing the mask. The box may be conventional in general structure, being closed by doors and having the mask projecting therefrom. Opening the doors by extracting the mask causes an oxygen feed cock to be opened.

The portion carried by the mask is constituted by a housing comprising a plurality of assembled-together parts having recesses and passages formed therein for defining a plurality of flow paths.

A first flow path connects an inlet 14 for oxygen under pressure to an outlet 16 leading to the mask. A second path connects an inlet 20 for dilution air to an outlet 22 leading to the mask. The flow rate of oxygen along the first path is controlled by an electrically-controlled cock. In the example shown, this cock is a proportional valve 24 under voltage control connecting the inlet 14 to the outlet 16 and powered by a conductor 26. It would also be possible to use an on/off type solenoid valve, controlled using pulse width modulation at a variable duty ratio.

A "demand" subassembly is interposed on the direct path for feeding dilution air to the mask, said subassembly acting to suck in ambient air and to detect the instantaneous demanded flow rate. This subassembly includes a pressure sensor 28 in the mask. In the example shown, the right section of the dilution air flow passage is defined between an altimeter capsule 30 of length that increases as ambient pressure decreases, and the end edge of an annular piston 32. The piston is subjected to the pressure difference between atmospheric pressure and the pressure that exists inside a chamber 34. An additional electrically-controlled valve 36 (specifically a solenoid valve) serves to connect the chamber 34 either to the atmosphere or else to the pressurized oxygen feed. The electrically-controlled valve 36 thus serves to switch from normal mode with dilution to a mode in which pure oxygen is supplied (so-called "100%" mode). When the chamber 34 is connected to the atmosphere, a spring 38 holds the piston in a position enabling the flow section to be adjusted by the altimeter capsule 30. When the chamber is connected to the supply, the piston presses against the capsule. The piston 32 can also be used as the moving member of a servo-controlled regulator valve.

The housing of the portion 10 also defines a breathe-out path including a breathe-out valve 40. The shutter element of the valve shown is of a type that is in widespread use at present for performing the two functions of acting both as a valve for piloting admission and as an exhaust valve. In the embodiment of FIG. 1, it acts solely as a breathe-out valve while making it possible for the inside of the mask to be maintained at a pressure that is higher than the pressure of the surrounding atmosphere by increasing the pressure that exists in a chamber 42 defined by the element 40 to a pressure higher than ambient pressure.

In a first state, an electrically-controlled valve 48 (specifically a solenoid valve) connects the chamber 42 to the atmosphere, in which case breathing out occurs as soon as the pressure in the mask exceeds ambient pressure. In a second state, the valve 48 connects the chamber to the pressurized oxygen feed via a flow rate-limiting constriction 50. Under such circumstances, the pressure inside the chamber 42 takes up a value which is determined by a relief valve 46 having a rated closure spring.

In the embodiment shown, the housing for the portion 10 carries means enabling a pneumatic harness of the mask to be inflated and deflated. These means are of conventional structure and consequently they are not described in detail. They comprise a piston 52 which can be moved temporarily by means of a lug 54 actuated by the user of the mask away from the position shown where the harness is in communication with the atmosphere to a position in which it puts the harness into communication with the oxygen feed 14. Nevertheless, these means also include a switch 56 moved by moving the lug 54 away from its rest position and performing a function that is described below.

The portion 12 of the regulator which is carried by the mask storage box includes a selector 58 that is movable in the direction of arrow f and is suitable for being placed in three different positions by the user.

In the position shown in FIG. 1, the selector 58 closes a normal-mode switch 60 (N). In its other two positions, it closes respective switches for 100% mode and for emergency mode (E).

The switches are connected to an electronic circuit 62 which operates, as a function of the selected operating mode, in response to the cabin altitude as indicated by a sensor 64 and in response to the instantaneous flow rate being demanded as indicated by the sensor 28 to determine the rate at which to supply oxygen to the wearer of the mask. The circuit card provides appropriate electrical signals to the first electrically-controlled valve 24.

In normal mode, the pressure sensor 28 supplies the instantaneous demand pressure to the outlet from the dilution air circuit into the mask. The circuit carried by an electronic card receives this signal together with information concerning the altitude of the cabin that needs to be taken into account and that comes from the sensor 64. The electronic card then determines the quantity or flow rate of oxygen to be supplied using a family of reference curves stored in its memory that take account both of instantaneous demand for flow rate and of cabin altitude, or that make use of a table having a plurality of entries, or even that perform calculations in real time on the basis of a stored algorithm.

The reference curves are drawn up on the basis of regulations that specify the concentration of the breathing mixture required for the pilot as a function of cabin altitude.

Figure 3:
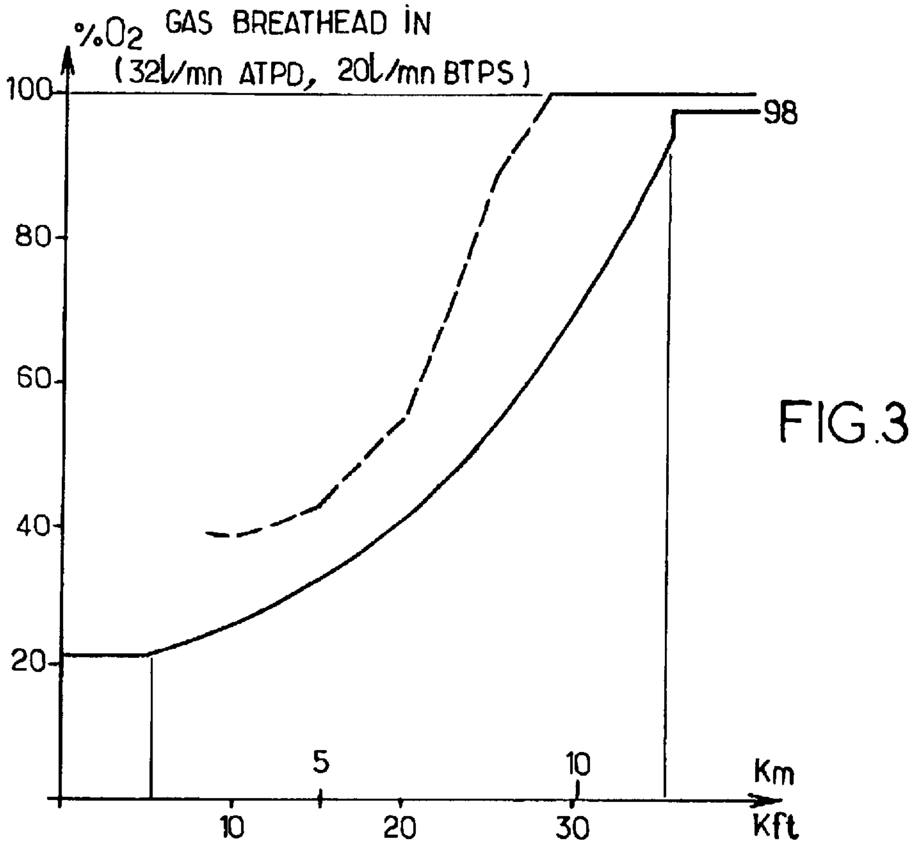
FIG. 3 is a graph plotting a typical curve for variation in oxygen flow rate as a function of cabin altitude and as required by regulations.

In FIG. 3, the continuous curve shows the minimum value for oxygen content required as a function of altitude. The dashed-line curve gives the maximum value. The reference curves are selected so as to avoid ever passing below the minimum curve. However, because of the flexibility provided by the electronic control, it is possible to approach very close to the minimum.

Figure 4:
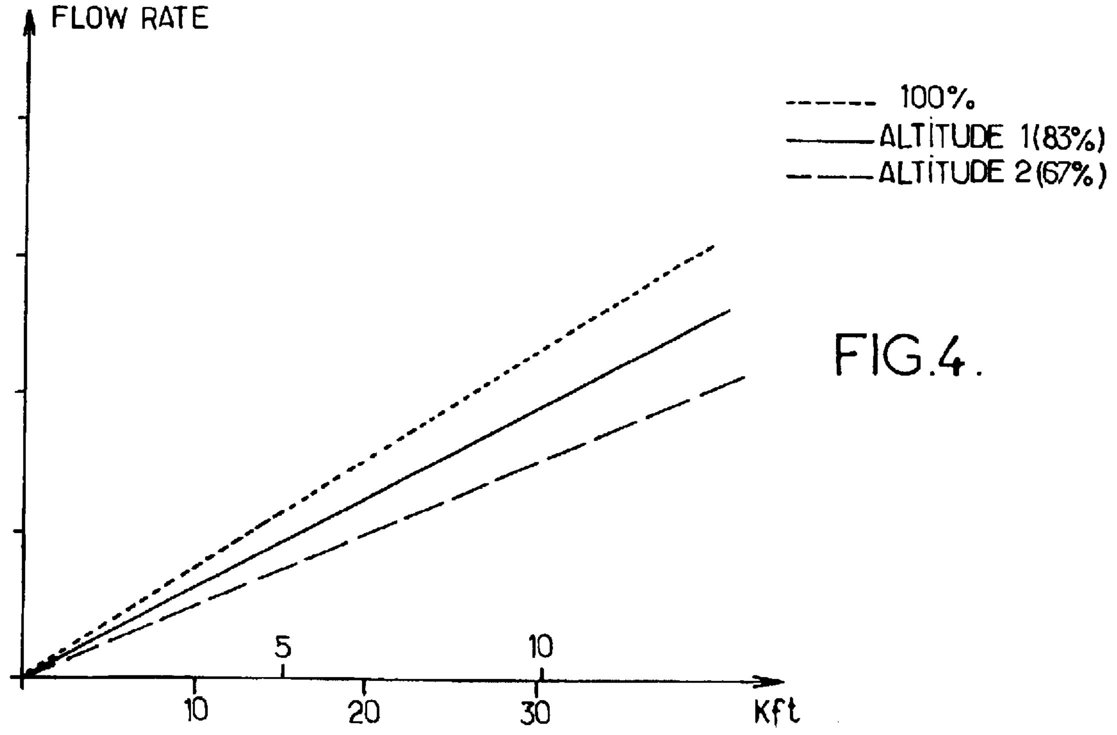
FIG. 4 is a graph plotting a set of curves showing variation in oxygen flow rate called for on breathing in at different cabin altitudes.

By way of example, FIG. 4 plots two curves showing oxygen flow rate variation and dilution air flow rate variation respectively as controlled by the electrically-controlled valve 24 and by the valve that is opened as a function of altitude depending on the value given by the signal supplied by the sensor 28.

In 100% mode, i.e. when the wearer of the mask moves the selector one notch to the right from the position shown in FIG. 1, the card 62 applies an electrical reference signal to the electrically-controlled valve 36. This causes the chamber 34 to be pressurized, pressing the piston 32 against the altimeter capsule 30 and closing off the dilution air inlet. The pressure sensor 28 detects the drop in pressure in the ambient air inlet circuit and delivers corresponding information to the card 62. The card then determines the oxygen flow rate to be delivered. The first electrically-controlled valve 24 then delivers the computed quantity of oxygen to the wearer of the mask.

When the wearer selects "emergency" mode by moving the selector 28 further to the right, the card 62 delivers an electrical reference to the electrically-controlled valve 48, which then admits pressure into the chamber 42, which pressure is limited by the release valve 46. As a general rule, the positive pressure that is established is about 5 millibars (mbar). Simultaneously, the dilution air inlet is interrupted as before. The pressure sensor 28 still delivers a signal to the card 62 which determines the quantity of oxygen that needs to be supplied in order to bring the pressure in the air inlet circuit up to a value equal to the rated value of the relief valve 46.

Figure 2:
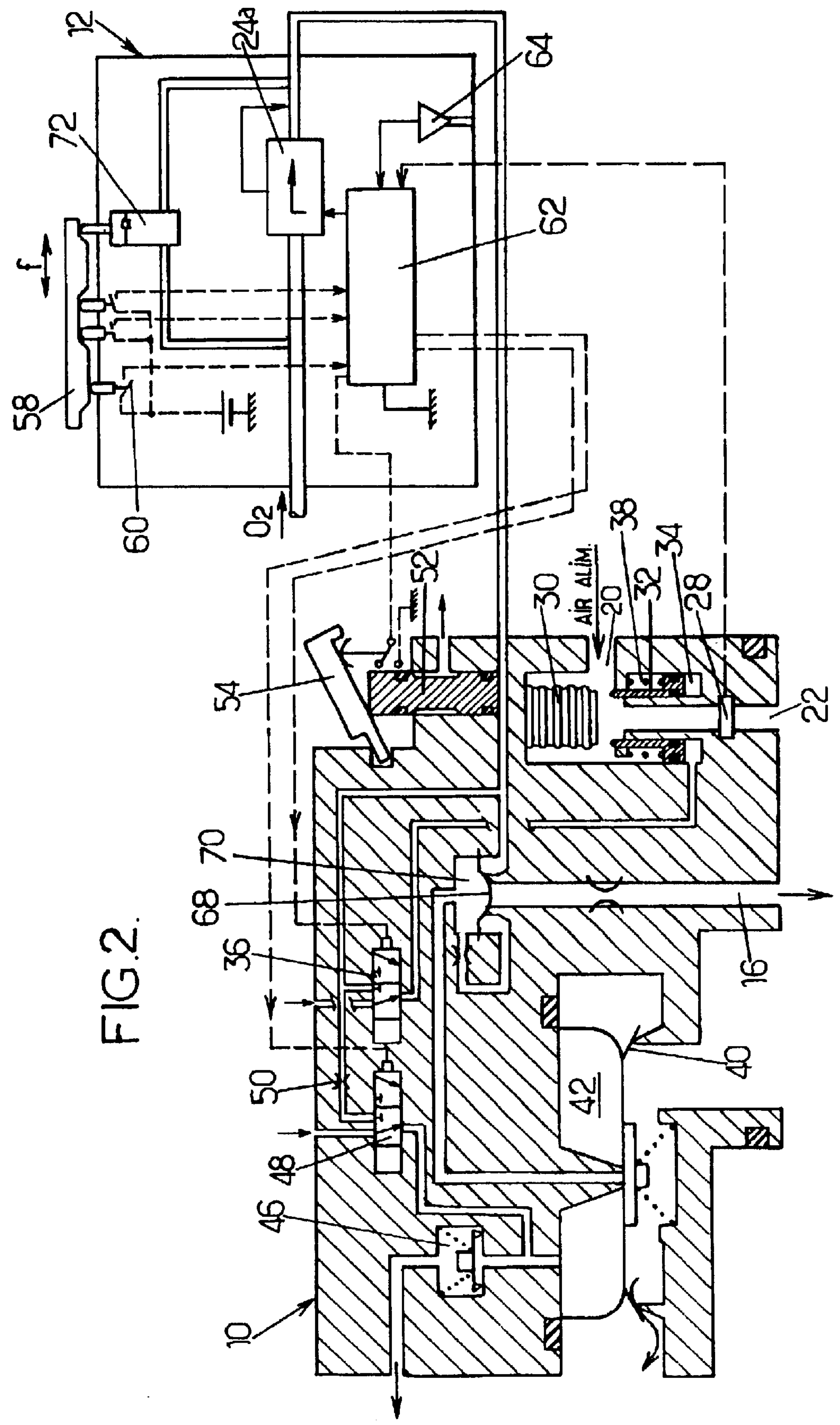
FIG. 2 is similar to FIG. 1 and shows a variant embodiment.

In the variant embodiment shown in FIG. 2, where members corresponding to those of FIG. 1 are designated by the same reference numerals, the first electrically-controlled valve 24 is placed in the housing of the mask storage box. The regulator can then be thought of as comprising a control portion located entirely in the box 12 and enabling an operating mode to be selected. A "demand" portion is located in the housing mounted on the mask and it performs the functions of taking in ambient air and of detecting the calling pressure. The third portion which supplies the additional oxygen required as a function of altitude and as a function of the breathe-in demand from the pilot, is now located in the housing in the mask storage box.

In the device shown in FIG. 2, the supply of additional oxygen via the electrically-controlled valve 24*a* is additionally controlled by a piloted pneumatic cock 68 of conventional structure, placed downstream from the electrically-controlled valve 24*a*. In conventional manner, the piloted pneumatic cock 68 is controlled by the pressure that exists in a pilot chamber 70. The membrane 40 which now performs both functions of pilot valve and of breathe-out valve controls the pressure in the pilot chamber 70.

The presence of a piloted cock in the embodiment of FIG. 2 makes it possible to provide a mechanically-controlled valve 72 which is controlled by the selector 58 so as to connect together the upstream and downstream ends of the electrically-controlled valve 24*a*. Thus, in the event of an electrical power supply failure, the wearer of the mask can immediately switch from oxygen-saving regulated mode to a conventional mode in which operation is purely pneumatic.

What is claimed is:

1. A method of regulating the flow rate of additional oxygen taken from a pressurized inlet for oxygen coming from a source and admitted into a breathing mask provided with an inlet for dilution ambient air, the method comprising:

measuring in real time the ambient pressure and the instantaneous inhaled breathe-in flow rate in terms of volume reduced to ambient conditions (directly or by measuring the rate at which dilution air is inhaled into the mask, while making allowance for the additional oxygen);

on the basis of the ambient pressure, determining the minimum oxygen content to be achieved in the complete inhalation phase in order to comply with respiratory standards; and controlling said instantaneous flow rate of additional oxygen in such a manner as to satisfy the requirements of the applicable standards with a safety margin that is generally a few percent.

2. A demand and dilution mask regulator comprising:

an oxygen feed circuit connecting a pressurized inlet for oxygen coming from a source and admitted into a breathing mask via a first electrically-controlled valve for directly controlling flow rate;

a dilution circuit supplying air from the atmosphere directly to the mask;

a breathe-out circuit including a breathe-out check valve connecting the mask to the atmosphere; and an electronic control circuit for opening the electrically-controlled valve for directly controlling flow rate as a function of signals supplied at least by a sensor of ambient atmospheric pressure and by a sensor of inhaled air flow rate or of inhaled total flow rate.

3. A device according to claim 2, wherein the electrically-controlled valve for directly controlling flow rate is of the progressively opening type or of the on/off type controlled by a pulse width modulated electrical signal having an adjustable duty ratio.

4. A device according to claim 2, wherein a control relationship stored in the electronic circuit is such that in normal operation the regulator supplies a flow rate of oxygen that is not less than that required for guaranteeing the oxygen content specified by regulations for cabin altitudes, said oxygen coming both from the source and from the dilution air.

5. A device according to claim 2, wherein the electronic circuit is designed to close a dilution valve in response to manual or automatic control.

6. A device according to claim 5, wherein the dilution valve is closed by means of a two-position valve which, in one state, causes said dilution valve to be closed by bringing a seat against a shutter carried by an element that is responsive to the pressure of the ambient atmosphere, and in the other state causes it to open.

7. A device according to claim 2, further comprising an additional electrically-controlled valve under manual or automatic control for maintaining positive pressure inside the mask by establishing positive pressure against the breathe-out valve tending to close it.

8. A device according to claim 2, wherein said oxygen feed circuit is located entirely in a housing fixed to the mask.

9. A device according to claim 2, wherein a portion of said oxygen feed circuit, including the first electrically-controlled valve, is integrated in a storage box for storing the mask in a ready position.

10. A device according to claim 2, wherein a pneumatically-piloted cock is placed on the oxygen feed circuit downstream from the first electrically-controlled valve.

11. A device according to claim 2, including a manual selector for selecting between operation with and without dilution and at positive pressure, the selector being carried by a mask storage box.

* * * * *